United States Patent
Rohde et al.

(10) Patent No.: US 6,303,345 B1
(45) Date of Patent: Oct. 16, 2001

(54) USE OF A VIRUS DNA AS PROMOTER

(75) Inventors: Wolfgang Rohde, Buseck; Dieter Becker, Köln, both of (DE); John W. Randles, Stirling (AU); Alain Hehn; Francesco Salamini, both of Köln (DE)

(73) Assignee: Max-Planck-Gesellschaft zur Forderung der Wissenschaften E.V., Berlin (DE)

( * ) Notice: Subject to any disclaimer, the term of this patent is extended or adjusted under 35 U.S.C. 154(b) by 0 days.

(21) Appl. No.: 09/462,975
(22) PCT Filed: Jul. 13, 1998
(86) PCT No.: PCT/EP98/04345
§ 371 Date: May 17, 2000
§ 102(e) Date: May 17, 2000
(87) PCT Pub. No.: WO99/04020
PCT Pub. Date: Jan. 28, 1999

(30) Foreign Application Priority Data

Jul. 16, 1997 (DE) .............................. 197 30 502

(51) Int. Cl.⁷ .......................... C12N 15/64; C12N 15/63; C07H 21/04
(52) U.S. Cl. ................... 435/91.4; 435/320.1; 536/23.1; 536/24.1
(58) Field of Search .............................. 435/235.1, 252.3, 435/320.1, 255.1, 254.11, 254.2, 252.1, 24.1, 419, 69.1, 91.4; 536/23.1, 24.1

(56) References Cited

U.S. PATENT DOCUMENTS 5,563,328   10/1996   Mitra et al. ........................ 800/294

FOREIGN PATENT DOCUMENTS

| 43 06 832 C 1 | 2/1994 | (DE) . |
| 4306832-C1 * | 2/1994 | (DE) . |
| 61257185A | 11/1986 | (JP) . |
| 63164888 | 7/1988 | (JP) . |
| WO 94/19472 | 9/1994 | (WO) . |
| WO-96/06932-A1 * | 3/1996 | (WO) . |

OTHER PUBLICATIONS

Rohde et al. Plant Mol. Biol. 27:623–628 1995.*

(List continued on next page.)

Primary Examiner—Robert A. Schwartzman
Assistant Examiner—Katharine F Davis
(74) Attorney, Agent, or Firm—Needle & Rosenberg, P.C.

(57) ABSTRACT

Described is the characterization and the use of strong viral promoters for expressing genes, in bacteria and fungi, in particular yeasts. The invention is based on the surprising finding that CFDV DNA (coconut foliar decay virus DNA) and CFDV DNA fragments contain a region which is active as promoter even in bacteria and fungi, in particular yeasts, although they are derived from a virus which infects monocotyledonous plants. The activity of the promoters described in *E. coli* is distinctly higher than that of the CaMV 35S promoter, which is also active in bacteria.

14 Claims, 4 Drawing Sheets

Figures 3, 4:
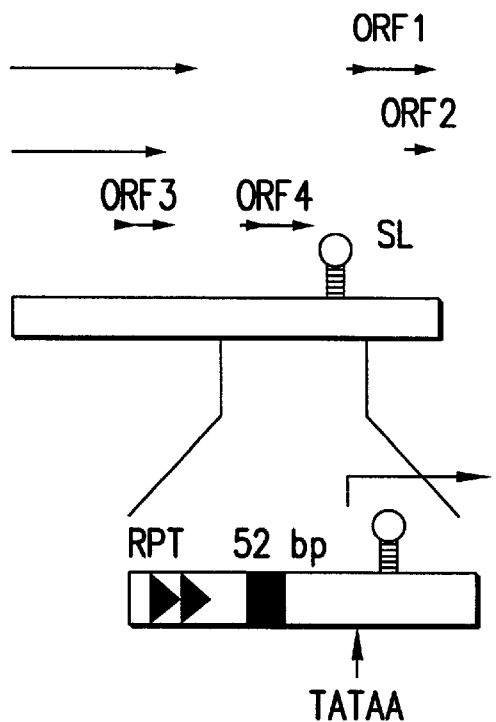

```
              A                           
           G     A                  A      
          C     G              G     A     
           C G                  C   G      
           G C                   C G       
           G C                   G C       
           A T                   G C       
           C G                   C G       
           C G                   C G       
           C G                   C G       
      ...CTG   A...         ...CTA   A... 
          RPT1                   RPT2      
```

OTHER PUBLICATIONS

Hehn and Rohde "Characterization of cis–acting elements affecting strength and phloem specificity of the coconut foliar decay virus promoter" *J of General Virology* 79:1495–1499, 1998.

Rohde et al. "The promoter of coconut foliar decay–associated circular single–stranded DNA directs phloem–specific reporter gene expression in transgenic tobacco" *Plant Molecular Biology* 27:623–628, 1995.

Mitra et al. "A Chlorella virus gene promoter functions as a strong promoter both in plants and bacteria" *Bio. and Biophy. Res. Commun.* 204(1):187–194, 1994.

Turner et al. "In vivo charactisation of a translational enhancer upstream from the coat protein open reading frame of potato virus S" *Arch Virol* 137:123–132, 1994.

Morozov et al. "Computer search of transcription control sequences in small plant virus DNA reveals a sequence highly homologous to the enhancer element of histone promoters" *DNA Sequence—J of Sequencing and Mapping* 4:395–397, 1994.

Randles et al. "Localisation of coconut foliar decay virus in coconut palm" *Ann. Appl. Biol.* 121:601–617, 1992.

Pobjecky et al. "Expression of the β–glucuronidase gene under the control of the CaMV 35S promoter in *Schizosaccharomyces pombe*" *Mol Gen Genet* 220:314–316, 1990.

Rohde et al. "Nucleotide Sequence of a Circular Single–Stranded DNA Associated with Coconut Foliar Decay Virus" *Virology* 176:648–651, 1990.

Fromm et al. "Inheritance and expression of chimeric genes in the progeny of transgenic maize plants" *Bio/Technology* 8:833–839, 1990.

Assaad and Signer "Cauliflower mosaic virus P35S promoter activity in *Escherichia coli*" *MGG* 223:517–520, 1990.

Davies and Stanley "Geminivirus genes and vectors" *TIG* 5(3):77–81, 1989.

Maas and Weer "Mechanism and optimized conditions for PEG mediated DNA transfection into plant protoplasts" *Plant Cell Reports* 8:148–151, 1989.

Töpfer et al. "Transient gene expression in tobacco protoplasts: II. Comparison of the reporter gene systems for CAT, NPT II, and GUS" *Plant Cell Reports* 7: 225–228, 1988.

Meyer et al. "A new petunia flower colour generated by transformation of a mutant with a maize gene" *Nature* 330:677–678, 1987.

Jefferson RA. "Assaying Chimeric Genes in Plants: The GUS gene fusion system" *Plant Molecular Biology Reporter* 5(4):387–405, 1987.

Negrutiu et al. "Fusion of a plant protoplasts: a study using auxotrophic mutants of *Nicotiana plumbaginifolia*, Viviani" *Theor Appl Genet* 72:279–286, 1986.

Deuschle et al. "Promoters of *Escherichia coli*: a hierarchy of in vivo strength indicates alternative structures" *EMBO J.* 5(11):2987–92, 1986.

Bradford MM. "A rapid and sensitive method for the quantitation of microgram quantities of protein utilizing the principle of protein–dye binding" *Analytical Biochemistry* 72:248–254, 1976.

* cited by examiner

FIG.1

```
      T   A   C
    A       T
    A       A
    T       G
    G       C
    G       C
    G       C
    G       C
    G       C
    C       G
    G       C
    C       G
    C       G
    C       G
    G       C
 ___A       T___
```

GEMINIVIRUSES: ---TAATATTAC---
CFDV: ---TAATACTAG--- (−)
---CTAGTATTA--- (+)

FIG.2

SEQUENCE LISTING

<160> NUMBER OF SEQ ID NOS: 7

<210> SEQ ID NO 1
<211> LENGTH: 1291
<212> TYPE: DNA
<213> ORGANISM: Artificial Sequence
<220> FEATURE:
<223> OTHER INFORMATION: Description of Artificial Sequence:/note=
      synthetic construct

<400> SEQUENCE: 1

| | | | | | |
|---|---|---|---|---|---|
| cgccaaaaac | ctctgctaag | tcccgtgcta | agtataaata | gccgcggggg | ctagtattac | 60 |
| ccccgcggct | ccccaacctc | tgctaacccc | gcttggctat | aaatgggttc | ctccattcgc | 120 |
| cgctggtgct | tcactctgaa | ctacgagaca | gaggaagagg | cggcgaatgt | tgtaaggcgc | 180 |
| atcgagtccc | ttaacttggt | ctatgctata | gttggggacg | aggttgcacc | ttcaactggc | 240 |
| caacgacacc | tccaaggatt | catccacttg | aagaccggtc | ggcgactgca | aggattgaag | 300 |
| actgttcttg | ggaatgacag | gattcacctg | gagccgaccc | gtggttccga | cgaacagaat | 360 |
| agagactact | gttcgaagga | acgggtgctt | ctcgagcacg | gagtcccgac | tcgtcctgga | 420 |
| gtcaaaaggc | cacgattggc | ccaacgattt | gctgaggaac | ctgatgaact | ccgcctggaa | 480 |
| gacccaggcg | ataccgaag | atgcgttgta | cacggagctt | cggtggaatg | gacaagatgg | 540 |
| gccgctgaaa | atccgttccc | atttccatat | cacaattggc | agcttgaagt | gctgtctgcg | 600 |
| atcggagagc | cagcggacga | tcgcacaatc | ctctggatat | gcggacgaga | cggaggagac | 660 |
| gggaagtccg | tgtttgccaa | atatctcgga | ctcaagcccg | actggttcta | cacatgtggt | 720 |
| ggaaccagaa | aggacgtatt | gtaccagtac | atcgaggacc | caaaacgaaa | tttaatcctc | 780 |
| gatgtaccca | ggtgtaattt | agagtattta | aattatgccc | tgttagaatg | tgttaagaac | 840 |
| agggcattca | gttcggacaa | atacgaaccc | cttagttatc | ttgggttcga | ccatgtgcat | 900 |
| gtactcgtat | ttgccaatgt | cctgcctgat | tatttgaaaa | tcagcaggga | cagaataaaa | 960 |
| ctgtggaata | tttaaagtat | gtgtcatcta | aattacacca | atacccgccc | gcccacgcgc | 1020 |
| tatcgtttac | atcttatgaa | tatcctgccc | aggccgaagg | cctgggaggt | gctaccggc | 1080 |
| cgaaggccgg | gaacaatatg | aatcgagtta | tgggcgggcc | cacaataaaa | gattccattt | 1140 |
| ggataagaac | gaatctgtta | ctttgcttgc | agtgcacgca | accactttcc | acgtcaccaa | 1200 |
| tccaggtgag | tagcttgctg | gagaagaaag | ccgcaagcct | ctatctaccg | tccatttgtt | 1260 |
| tttgcgcgat | cggacggctg | agttgatctg | g | | | 1291 |

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence:/note=
      synthetic construct

<400> SEQUENCE: 2
agccgcgggg gtaatactag cccccgcggc t                                         31

<210> SEQ ID NO 3
<211> LENGTH: 9
<212> TYPE: DNA
<213> ORGANISM: Artificial Sequence
<220> FEATURE:
<223> OTHER INFORMATION: Description of Artificial Sequence:/note=

-continued

```
        synthetic construct

<400> SEQUENCE: 3 taatattac                                                              9

<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence:/note=
        synthetic construct

<400> SEQUENCE: 4 taatactag                                                              9

<210> SEQ ID NO 5
<211> LENGTH: 9
<212> TYPE: DNA
<213> ORGANISM: Artificial Sequence
<220> FEATURE:
<223> OTHER INFORMATION: Description of Artificial Sequence:/note=
        synthetic construct

<400> SEQUENCE: 5 ctagtatta                                                              9

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:/note=
        synthetic construct

<400> SEQUENCE: 6
ctgcccaggc cgaaggcctg gga                                             23

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:/note=
        synthetic construct

<400> SEQUENCE: 7
ctacccggcc gaaggccggg a                                               21
```

USE OF A VIRUS DNA AS PROMOTER

It is generally known that genetic engineering techniques allow individual genes to be transferred into the genome of organisms, such as microorganisms, yeasts or plants, in a targeted manner. This technique, which is known as transformation or, in the case of higher cells, also as transfection, is carried out routinely by various routes, for example by particle gun bombardment (cf. M. E. Fromm, F. Morrish, C. Armstrong, R. Williams, J. Thomas and T. M. Klein: "Inheritance and expression of chimeric genes in the progeny of transgenic maize plants", Bio/Technology 8: 833–839, 1990), naked DNA transfer (cf. P. Meyer, I. Heidmann, G. Forkmann and H. Saedler: "A new petunia flower colour generated by transformation of a mutant with a maize gene", Nature 330: 677–678, 1987) or by Agrobacterium-mediated stable integration of genes or gene segments into the genome of a recipient plant. As an alternative for the chromosomal integration of foreign genes, it is possible, for example, to use extrachromosomally replicating vectors in order to express foreign genes in a desired organism without integration. Examples of extrachromosomally replicating vectors which are available for plants are those developed from plant viruses (cf., for example, J. W. Davies and J. Stanley: "Geminivirus genes and vectors", Trends Genet. 5: 77–81, 1989). To do this, the foreign genes to be expressed in the chosen organisms must be brought under the control of regulatory signals (promoter, terminator) which are suitable for this organism and which ensure constitutive or inducible and/or optionally tissue- and/or development-specific transcription. Moreover, it is desirable to provoke an increased mRNA synthesis of the foreign gene by using a strong promoter.

It is known that there are great differences between the regulation signals of the transcription of genes to be expressed which are found in bacteria and eukaryotes (cf., for example, Mitra et al., 1994, Biochem. Biophys. Res. Commun. 204: 187–194; Pobjecky et al., 1990, Mol. Gen. Genet. 220: 314–316). Although, with regard to promoters, eukaryotes also contain a TATA or Hogness box which is very similar and corresponds to the -10-sequence of the prokaryotes (TATAAT), this box is further away from the transcription start in the case of eukaryotes. Additional elements exist in the eukaryotes which are vital for the promoter activity. This is why promoters derived from eukaryotes are, as a rule, unsuitable for regulating the transcription of genes in prokaryotes and vice versa. Also, differences between the promoter structures exist within the eukaryotes, for example between plants and fungi, and also, for example, with regard to the specificity of a promoter for specific cells within one and the same eukaryotic organism.

It would therefore be exceedingly useful for industry and research to have available promoters which are equally active in prokaryotes and eukaryotes, for example in bacteria, fungi and plants. For example, this would dispense with complicated recloning work when it is intended to employ, at the same time, prokaryotic and eukaryotic recipient organisms for the expression of foreign genes.

Such a promoter is the 35S RNA promoter of the cauliflower mosaic virus (CaMV). This promoter meets the requirements made on a strong constitutive promoter in plant cells and is employed predominantly for the transformation of plants, (cf., R. Walden: "Genetic Transformation in Plants", Open University Press, Milton Keynes, 1988). However, it is known that the CaMV 35S promoter is also active in bacteria (Assaad and Signer, Molecular and General Genetics 223: 517–520, 1990).

Accordingly, it is an object of the invention to provide further promoters derived from a plant specific virus which are active in bacteria and/or fungi. Advantageously, they are active both in plants and, in particular, equally in plants and/or fungi, and bacteria so that they can be employed not only in eukaryotes, but also in prokaryotes. In addition, they advantageously also have a higher promoter activity in plants, fungi and/or bacteria compared with the CaMV 35S promoter.

The German patent DE 43 06 832 of the Max-Planck-Gesellschaft zur Förderung der Wissenschaften and Rohde et al., Plant Molecular Biology 27: 623–628, 1995 have described the use of a DNA which is derived from the CFDV virus (coconut foliar decay virus), which attacks the coconut palm *Cocos nucifera,* and whose structure is shown in FIGS. 1, 3A and 3B of the Patent Specification as a viral phloem-specific promoter for the tissue-specific expression of genes in transgenic plants.

The CFDV virus is located in the vascular system of the plant (cf. J. W. Randles et al.: "Localization of coconut foliar decay virus in coconut palm", Ann. Appl. Biology 1992, 601–617). A DNA associated with the disease symptoms and the occurrence of viral particles has already been cloned, sequenced and its structure determined at an earlier point in time (cf. W. Rohde et al.: "Nucleotide sequence of a circular single-stranded DNA associated with coconut foliar decay virus", Virology 176: 648–651, 1990). CFDV is a viral phytopathogen with a genome consisting of covalently closed-circular simplex DNA. Rohde et al., Virology 176: 648–651, 1990 described a DNA molecule of CFDV with a size of 1291 nucleotides (SEQ ID NO:1) and deletion mutants thereof. CFDV is not a representative of the geminivirus group, but probably constitutes the prototype of the DNA virus group of the "circoviruses".

Surprisingly, it has now been found that the CFDV-DNA and fragments of the CFDV-DNA are also active as promoters in bacteria and fungi. Thus, for example, the promoter activity in *E. coli* is markedly higher than that of the CaMV 35S promoter which is also active in bacteria (Assaad and Signer, Molecular and General Genetics 223: 517–520, 1990); the CFDV constructs pRT CF4 and pRT CF9 even show an activity in *E. coli* which is up to 60 times higher than that of the CaMV 35S promoter; in tobacco protoplasts too, the CDFV fragment promoter which is contained in the construct pRT CF4 shows a slightly higher promoter activity than the CaMV 35S promoter. It is because of this activity that the CFDV promoters are suitable, in particular, for use in bacterial systems and fungal systems, for example for the generation of pharmacologically active proteins or peptides.

Accordingly, the object of the invention is the use, characterized in the claims, of the CFDV-DNA and of CFDV-DNA fragments as bacterial promoters and promoters in the fungi, in particular in yeasts.

To generate the CFDV-DNA fragments which are suitable for the use according to the invention, techniques which are well known to the skilled worker are used, such as, for example, suitable cleavage sites of the restriction endonucleases on the CFDV-DNA, or the polymerase chain reaction technique, which allows, starting from a full-length CFDV-DNA construct, CFDV-DNA fragments of the desired length to be amplified using a specific primer. To this end, the primers which suit the CFDV fragment are synthesized in a manner known per se using the nucleotide sequence of the CFDV virus described by W. Rohde et al. in Virology 176: 648–651, 1990 and, more specifically, the nucleotide sequences in the region of the 5' or 3' ends of the desired fragment.

CFDV DNA fragments which are preferred for the use according to the invention are the DNA fragments with the nucleotides 211 to 991, 409 to 991, 611 to 991, 711 to 991, 211 to 962, 409 to 962, 611 to 962 and 711 to 962 and the XhoI/StyI fragment of the CFDV DNA with the nucleotides 1 to 1157 of SEQ ID NO:1.

CFDV DNA fragments which are very particularly preferred for the use according to the invention are DNA fragments which only encompass the sequence section of the CFDV DNA including the repeated sequence (RPT), the 52 bp sequence and the TATAA box, without encompassing the sequence section up to the end of the open reading frame ORF1 and all of the nucleotides required for constructing the so-called stem-loop structure. Accordingly, very particularly preferred DNA fragments are the DNA fragments with the nucleotides 611 to 991 and 611 to 962.

Equally, the invention relates to the use according to the invention of CFDV DNA derivatives or CFDV fragment derivatives which are derived from the CFDV DNA or from CFDV fragments by substituting, deleting, inserting or modifying individual nucleotides or smaller groups of nucleotides and have a promoter activity which is comparable with that of the CFDV DNA or the starting fragments. A comparable promoter activity can be, for example, a promoter activity which is up to 20% higher or lower than that of the CFDV DNA or of the starting fragment.

The figures show:

FIG. 1: the schematic structure of the CFDV DNA with six possible open reading frames (ORF1–6) and the so-called stem-loop structure. The arrow indicates the XhoI cleavage site.

FIG. 2: the so-called stem-loop structure (SEQ ID NO:2); it shows homology to a similar structure in the genome of geminiviruses and is probably responsible for the replication of the virus (SEQ ID NO:3, SEQ ID NO:4, and SEQ ID NO:5).

FIG. 3: the schematic arrangement of possible signals for transcriptional regulation on the CFDV DNA which has been linearized by cleavage at the XhoI cleavage site. The arrows indicate the larger open reading frames ORF1, ORF2, ORF3 and ORF4 on the CFDV DNA. The position marked "TATAA" comprises a possible TATA box, and the abbreviation RPT, which is assigned to two arrow heads, suggests a repeated sequence; the stem-loop structure is marked "SL".

FIG. 4: the sequence of the two repeated sequences (RPT) and their arrangement as stable stem-loop structures with the customary CGAAG-loop sequence (SEQ ID NO:6 and SEQ ID NO:7).

Figure 5:
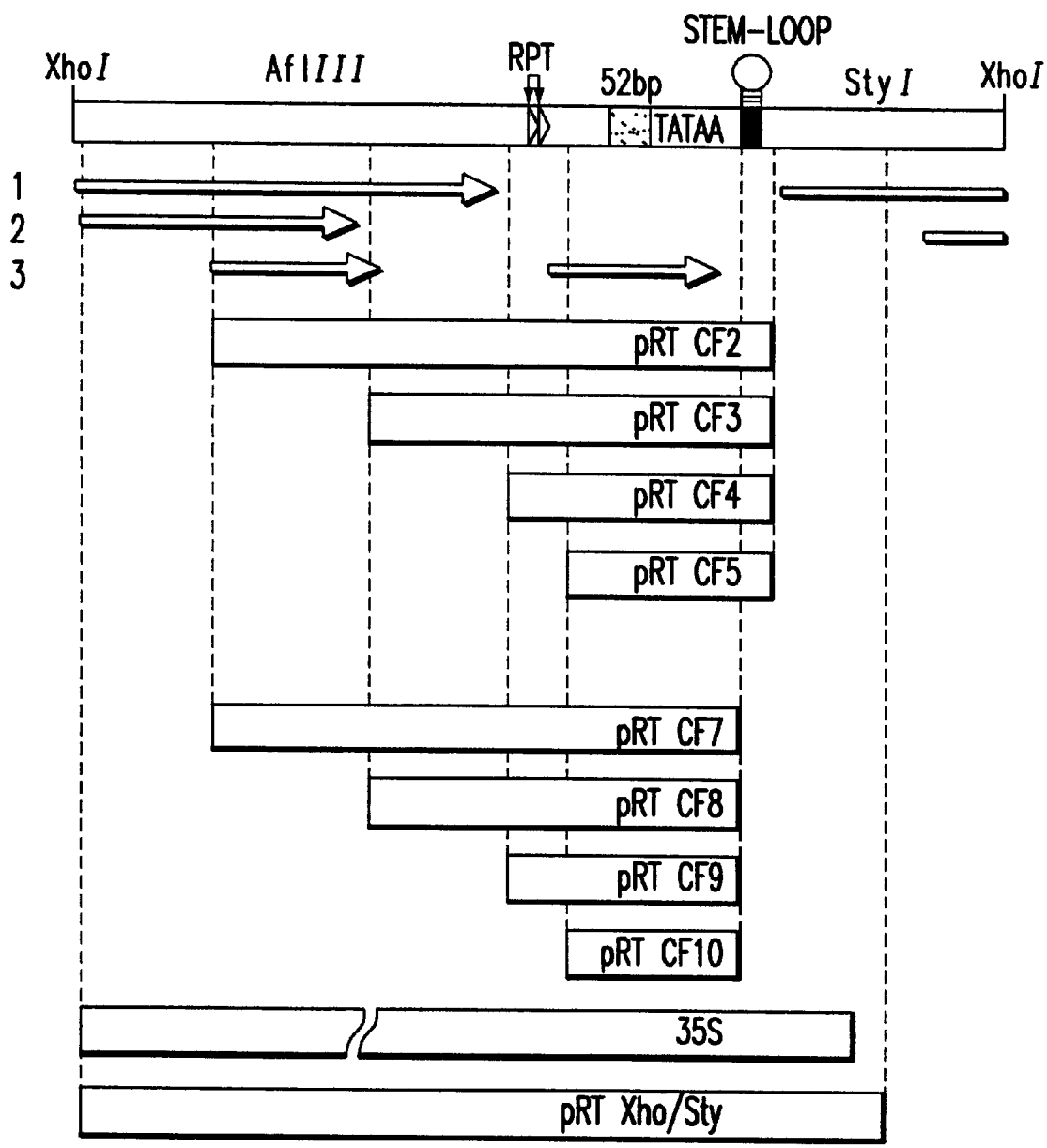

FIG. 5: a schematic representation of the position, on the CFDV DNA linearized by cleavage at the XhoI cleavage site, of various CFDV fragments used for constructs for determining promoter strength. The arrow heads show the position of the two directly repeated sequences (RPT) upstream of a 52 bp element (black box). This element shows 70% sequence identity between CoYMV and CFDV. The arrows indicate larger open reading frames in the three reading frames 1, 2 and 3 (ORF1, ORF2, ORF3) of the CFDV DNA. The abbreviation TATAA suggests a possible TATA box, and the position of the stem-loop structure is also given. XhoI, AflIII and StyI mark the position of cleavage sites for restriction endonucleases.

Figure 6:
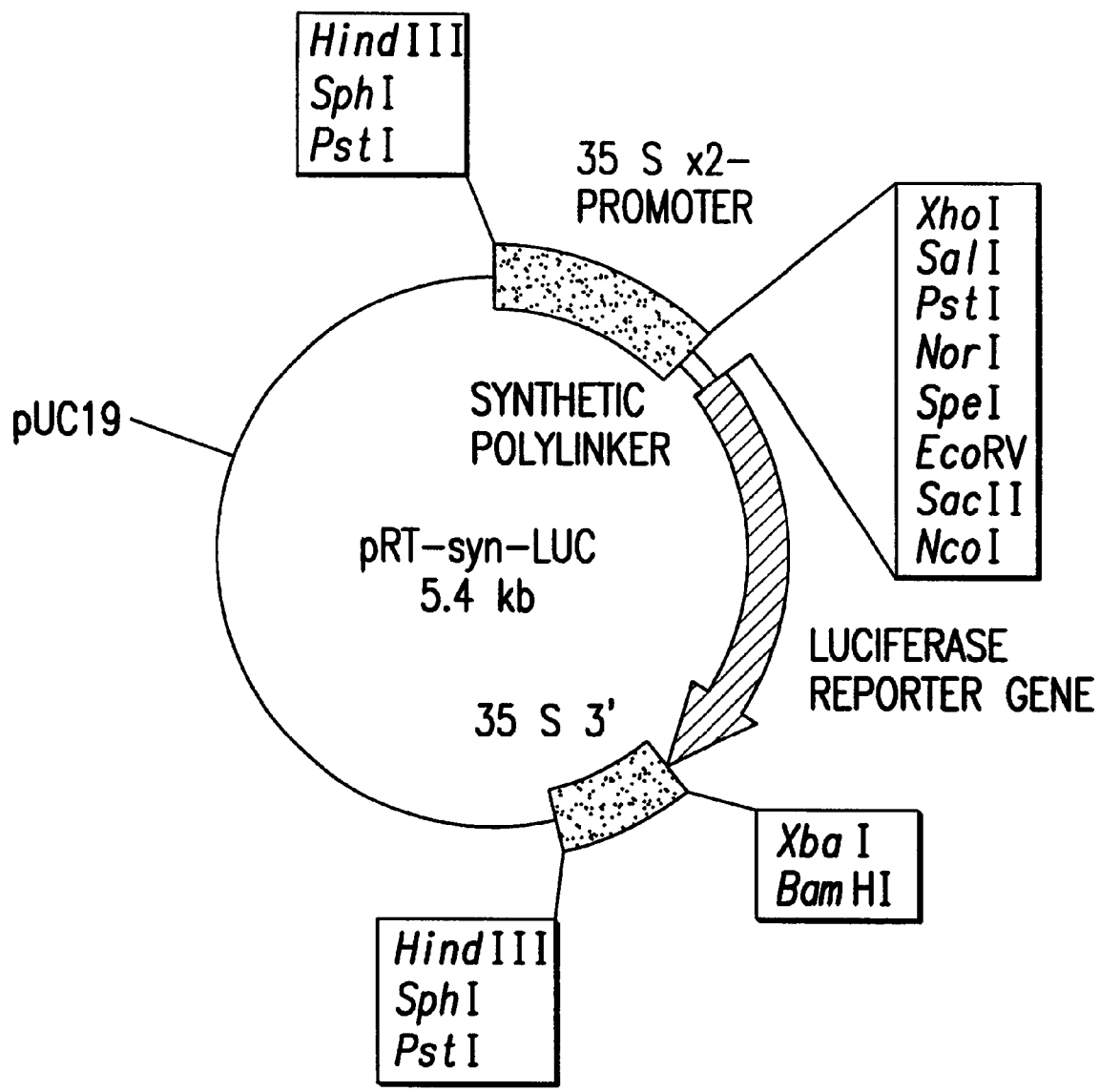

FIG. 6: the schematic structure of the starting plasmid pRTsynLUC.

STUDIES ON THE PROMOTER STRENGTH OF VARIOUS CFDV FRAGMENTS IN PLANTS AND BACTERIA

In order to study promoter region and promoter strength by the transient expression in plant cells and bacteria, fragments of the CFDV DNA, for which it was not possible to fall back on suitable restriction cleavage sites on the CFDV DNA, were first amplified, starting from a full-length CFDV construct (Rohde et al., Plant Mol. Biol. 27: 623–628, 1995) by means of the polymerase chain reaction (PCR) and, as subgenomic fragments, fused transcriptionally with the β-glucuronidase gene (GUS) in the plasmid vector pRT2synGUSΔH.

The constructs which contain the β-glucuronidase gene fused to the full CFDV sequence or the XhoI/StyI fragment of the CFDV DNA were prepared as described in DE 43 06 832. The resulting plasmids were compared in transient expression experiments with a similar CaMV 35S construct.

USE EXAMPLE

Unless otherwise specified, all of the process steps given hereinbelow were carried out following standard procedures as they are described, for example, in Sambrook et al., Molecular Cloning, A Laboratory Manual, Cold Spring Harbor Laboratory, Cold Spring Harbor, N.Y., USA (1989).

I. Generation of CFDV (Fragment) GUS Constructs for Transient Expression

For constructs with CFDV fragments for which it was not possible to fall back on suitable restriction cleavage sites on the CFDV DNA, the starting plasmid used was the full-length CFDV construct described by Rohde et al. in Plant Mol. Biol. 27: 623–628, 1995. The CFDV genome was amplified with the aid of specific primers which contained additional restriction cleavage sites, viz. HindIII for the 5'-end and NcoI for the 3'-end of the amplified DNA molecules. Depending on the choice of the primers, CFDV fragments were obtained whose length was fixed. The primers were synthesized with reference to the nucleotide sequence of the CFDV virus described by W. Rohde et al. in Virology 176: 648–651, 1990, more specifically with the aid of the nucleotide sequences in the region of the 5'- and 3'-ends of the desired fragment in order to obtain the CFDV fragments given in Table 1 below by subsequent DNA amplification. In addition, DNA sections were added, to the primers, which contained the abovementioned additional restriction cleavage sites.

The amplification products were digested with HindIII/NcoI, and the cleavage products were separated in an agarose gel and the desired DNA fragments isolated by electroelution.

The CFDV fragments were then ligated into vector pRT2synGUSΔH which had previously been prepared from the plasmid pRTsynLUC (FIG. 6; Turner et al., Arch. Virol. 137: 123–132, 1994). To this end, the luciferase gene was removed by NcoI/BamHI digestion and replaced by the GUS gene with NcoI/BamHI ends. Finally, the HindIII cleavage site was deleted on the 35S 3'-end by partially cleaving the plasmid with HindIII, filling in the cleavage site and circularizing the linear molecule by religation to give pRT2synGUSΔH. An NheI cleavage site was thus created instead of the HindIII cleavage site. The 35S promoter was removed from this plasmid by digestion with HindIII/NcoI and replaced by the corresponding HindIII/NcoI CFDV fragments.

The constructs which contain the β-glucuronidase gene fused to the full CFDV sequence or the XhoI/StyI fragment of the CFDV DNA were prepared as described in DE 43 06 832, chapter "Studies on promoter region and promoter strength", and Chapter I.2 of the use example. To this end, the CFDV cDNA, which is 1291 nucleotides in size (cf. Rodhe et al., Virology 176: 648–651, 1990), was excised from a plasmid using the restriction enzyme XhoI and, either as the full sequence or after additional digestion with the restriction endonuclease StyI after separation in the agarose gel and electroelution as subgenomic fragments, fused transcriptionally with the β-glucuronidase gene in the plasmid vector pUC19GUS. To construct pUC19GUS, the vector pUC103GUS was used as starting material, and this was prepared from the vector pRT103GUS (Töpfer, R., Pröls, M., Schell, J. and Steinbiss, H. H., Plant Cell Rep., 1988, 7: 225–228) by digestion with PstI and subcloning the GUS fragment in pUC19 (PstI). The CaMV35S promoter was removed from pUC103GUS by digestion with the restriction enzymes HindIII and XhoI, and its ends were converted into flush ends. From this, the relevant constructs were prepared by covalent linkage with the linearized full CFDV sequence obtained above, or the StyI fragment, using T4-induced DNA ligase.

The CFDV fragments contained as promoters in the generated CFDV fragment GUS constructs are shown with respect to their exact position on the CFDV DNA in Table 1 and, diagrammatically, in FIG. 4. The nucleotide positions indicated in Table 1 relate to a CFDV DNA which had been linearized by cleavage with the restriction endonuclease XhoI and whose 5' end had been assigned the position 1. Finally, the corresponding DNA sections for the stem-loop structure, the open reading frames ORF1 and ORF2 and other structural elements of the CFDV DNA were also included.

The CFDV fragments contained in Table 1 and shown schematically in FIG. 4, which are marked "pRT CF2–5", all retain the 52 bp sequence(nucleotides 734 to 785 of SEQ ID NO:1), the TATAA box and the so-called stem-loop structure of the CFDV DNA. The CFDV fragments marked "pRT CF7–10" are CFDV fragments all of which still contain the 52 bp sequence and the TATAA box, that have the 3' end of the CFDV sequence deleted in such a way that formation of the stem-loop structure is no longer possible. The CFDV fragments termed pRT CF4 and 9 both additionally contain the RPT sequences, and the CFDV fragments termed pRT CF2, 3, 7 and 8 extend even further in the 5' direction.

TABLE 1

| CONSTRUCT | 5' end of the CFDV fragment | 3' end of the CFDV fragment |
|---|---|---|
| pRT CF2 | 211 | 991 |
| pRT CF3 | 409 | 991 |
| pRT CF4 | 611 | 991 |
| pRT CF5 | 711 | 991 |
| pRT CF7 | 211 | 962 |
| pRT CF8 | 409 | 962 |
| pRT CF9 | 611 | 962 |
| pRT CF10 | 711 | 962 |
| pRT XhoI/StyI | 1 | 1157 |
| RPT1 | 655 | 676 |
| RPT2 | 682 | 701 |
| 52-bp-sequence | 734 | 785 |
| TATA-box | 934 | 939 |
| SL | 941 | 971 |
| ORFI | 1004 | 583 |
| ORF2 | 1215 | 3.83 |

The construct pRT 35S, which contains the GUS reporter gene fused to the CaMV 35S promoter and which is employed for comparison purposes was prepared as described in German Patent P 43 06 832 as vector pUC103GUS from vector pRT103GUS (Töpfer, R., Pröls, M., Schell, J. and Steinbiss, H. H., Plant Cell Rep., 1988, 7: 225–228) by PstI digestion and subcloning the GUS fragment into pUC19 (PstI).

II. Transient Expression of CFDV Fragment GUS Constructs in E. coli
II.1. Transformation of E.coli
Competent E.coli JM109 cells were transformed with the relevant plasmid DNAs by electroporation and selected on LB plates (with added ampicillin).
III.2 Analysis of the E.coli Transformations
Single colonies were allowed to grow overnight in 2 ml of LB medium (with added ampicillin). Batches of 10 μl bacterial suspension were disrupted with 35 μl of extraction buffer (50 mM sodium phosphate buffer, pH 7; 10 mM EDTA, 0.1% Triton X-100), 5 μl of 10× 4-MUG solution were added (4-MUG: 4-methylumbelliferyl-β-D-glucuronide; cf. R. A. Jefferson: "Assaying chimeric genes in plants: the GUS gene fusion system", Plant Mol. Biol. Rep. 5: 387–405, 1987), and the batches were incubated for 10 minutes at 37° C. or, to measure the course over time of the GUS activity, for 10 minutes, 20 minutes or 47 minutes at 37° C. The reaction was stopped by adding 1 ml of 0.2 M Na₂CO₃ buffer, and the GUS activity was determined fluorimetrically using 4-methylumbelliferyl-β-D-glucuronide. The protein was analysed quantitatively by the method of Bradford (cf. M. Bradford: "A rapid and sensitive method for the quantitation of microgramme quantities of protein utilizing the principle of protein dye binding", Anal. Biochem. 72: 248–254, 1976).

The results obtained for the individual constructs are given in Tables 2A and 2B which follow. The results in Table 2A are shown as the percentage activity based on the activity of the CFDV promoter construct pRT CF4, which, being the highest promoter activity achieved in this example, was set at 100%. The results of two or three independent experiments and the mean value from these experiments are given. The percentages shown for the individual incubation times in Table 2B in the right-hand column in each case indicate the percentage activity based on that of the CFDV promoter construct pRT CF4, corresponding to the absolute values shown for selected constructs in the left-hand columns in each case.

TABLE 2A

| CONSTRUCT | Exp. 1 | Exp. 2 | Exp. 3 | Mean value |
|---|---|---|---|---|
| pRT CF2 | 4.4 | 15.8 | 17.1 | 12.4 |
| pRT CF3 | 5.7 | 14.0 | 12.6 | 10.7 |
| pRT CF4 | 100 | 100 | 100 | 100 |
| pRT CF5 | 5.1 | 14.9 | — | 10.0 |
| pRT CF7 | 17.3 | 11.5 | 7.9 | 12.2 |
| pRT CF8 | 12.4 | 24.2 | 25.7 | 20.7 |
| pRT CF9 | 84.4 | 111.7 | 141.8 | 112.6 |
| pRT CF10 | 4.0 | 11.3 | 26.7 | 14.0 |
| pRT CF XS | 6.6 | 20.8 | 15.9 | 14.4 |
| pRT 35S | 3.6 | 11.3 | 8.6 | 7.8 |

TABLE 2B

| CONSTRUCT | Incubation for 10 minutes | | Incubation for 20 minutes | | Incubation for 47 minutes | |
|---|---|---|---|---|---|---|
| pRT CF4 | 35 560 | 100 | 78 900 | 100 | 407 400 | 100 |
| pPT CF5 | 1 396 | 3.9 | 2 900 | 3.6 | 12 980 | 3.2 |
| pFT CF9 | 27 650 | 77.7 | 75 900 | 96.2 | 405 500 | 99.5 |
| pRT CF XS | 2 040 | 5.7 | 4 820 | 6.1 | 37 400 | 9.2 |
| pRT 35S | 1 222 | 3.4 | 1 766 | 2.2 | 6 820 | 1.7 |

The results shown in Table 2A demonstrate that all of the CFDV DNA fragments mentioned also act as promoters in bacteria and, when incubated for 10 minutes, show a higher activity than the CaMV 35S promoter (cf. construct pRT 35S). Compared with construct pRT CF4, which, as promoter, contains a CFDV DNA fragment which encompasses the repeated sequence (RPT), the 52 bp sequence, the TATAA sequence and the stem-loop structure in the region of the nucleotides 941 to 971, but no DNA sections whatsoever of the open reading frames ORF1, ORF2 and also ORF3, construct pRT 35S, which contains the CaMV 35S promoter, only shows less than 10% of the activity of the former.

Construct pRT CF9, which differs from construct pRT CF4 by the fact that it encompasses a CFDV fragment which is deleted on the 3' end of the sequence in such a way that the stem-loop structure can no longer be found, shows a similarly high activity. Accordingly, formation of the stem-loop structure does not seem to be necessary for the above-mentioned fragments to act as promoters in bacteria.

With increasingly long incubation (Table 2B), the activity of most of the CFDV fragment GUS constructs shown in Table 2B increases, while that of the CaMV 35S promoter remains constantly at a very low level. At the end of the 47-minute incubation time, the CaMV 35S promoter now only has approximately 2% of the activity of the CFDV fragment promoters of the constructs pRT CF4 and 9.

III. Transient Expression of CFDV fragment GUS Constructs in Tobacco Protoplasts III.1. Protoplast Media

| K3: | Macro elements: | Micro elements: |
|---|---|---|
| | 25 mM $KNO_3$ | 100 $\mu$M $H_3BO_3$ |
| | 1 mM $NaH_2PO_4$ | 130 $\mu$M $MnSO_4$ |
| | 6 mM $CaCl_2$ | 40 $\mu$M $ZnSO_4$ |
| | 3 mM $NH_4NO_3$ | 5 $\mu$N KCl |
| | 1 mM $(NH_4)_2SO_4$ | 1 $\mu$M $CuSO_4$ |
| | 1 mM $MgSO_4$ | 1 $\mu$M $CoCl_2$ |
| | Iron in EDTA: | Vitamin solution: |
| | 1 $\mu$M $FeSO_4$ | 270 $\mu$M glycine |
| | 1 $\mu$M $Na_2$EDTA | 160 $\mu$M nicotinic acid |
| | | 100 $\mu$M pyridoxin |
| | | 3 $\mu$M thiamine |
| | Carbohydrates: | Hormones: |
| | 400 mM sucrose | 5.5 $\mu$M NAA |
| | 1.7 mM xylose | 1.0 $\mu$M kinetin |
| | 0.5 mM inositol | |
| | pH 5.6 osmotic value: 600 mOs | |
| W5: | 150 mM NaCl | |
| | 125 mM $CaCl_2$ | |
| | 5 mM KCl | |
| | 5 mM glucose | |
| | pH 5.6–6.0 | |
| MaMg: | 450 mM mannitol | |
| | 15 mM $MgCl_2$ | |
| | 0.1% MES | |
| | pH 5.6 | |

III.2. Preparation of Tobacco Protoplasts (cf. I. Negrutiu et al., "Fusion of plant protoplasts: a study using auxotrophic mutants of *Nicotiana plumbaginifolia, viviani*", Theor. Appl. Genet. 72: 279–286, 1987).

Leaves (10 g) of tissue-culture-grown *Nicotiana tabacum* plants (var. SR1) were incubated in 100 ml of enzyme solution for 16 hours at 25° C. in the dark, and the resulting protoplasts were separated from coarse tissue residues by screens (mesh size 100 $\mu$M). The protoplasts were purified further by repeated centrifugations and washing with K3 medium, during which process the viable protoplasts concentrated in each case at the surface, and, finally, by resuspension in W5 medium and sedimentation by centrifugation. The protoplast sediment was taken up in MaMg buffer and brought to a concentration of $10^6$/ml.

III.3. Protoplast Transformation (cf. C. Maas and W. Werr: "Mechanism and optimized conditions for PEG mediated DNA-transfection into plant protoplasts", Plant Cell Rep. 8: 148–151, 1989).

15 $\mu$l of plasmid/carrier DNA (corresponding to 10 $\mu$g of CFDV fragment GUS construct or CaMV 35S GUS plasmid DNA and 50 $\mu$g of calf thymus DNA) were added to 500-$\mu$l batches of protoplasts, and the suspension was incubated for ten minutes at room temperature, then carefully underlaid with PEG solution (40% PEG 4000, 0.1 M $Ca(NO_3)_2$, 0.4 M mannitol) and immediately rotated until all the streaks had disappeared. After incubation for a further 30 minutes, 4 ml of K3 medium (with antibiotics and kinetins) were added, and the individual transformation batches were kept for 20 hours at 25° C. in the dark.

III.4. Analysis of the Protoplast Transformations

After 20 hours, the protoplast batches were made up to 10 ml with W5 medium, centrifuged, the sedimented protoplasts were resuspended in 1 ml of W5 medium and then recentrifuged, and frozen in liquid nitrogen. To determine the protein quantity and GUS enzyme activity, the protoplasts were comminuted in a pestle and mortar in 50 $\mu$l of GUS extraction buffer, and the GUS activity was determined fluorimetrically with 4-methylumbelliferyl-$\beta$-D-glucuronide (4-MUG; cf. R. A. Jefferson, Plant Mol. Biol. Rep. 5: 387–405, 1987). To this end, the batch was incubated with 4-methylumbelliferyl-$\beta$-D-glucuronide (4-MUG) for 1 hour at 37° C. The protein quantity was determined by the method of Bradford (cf. M. Bradford, Anal. Biochem. 72: 248–254, 1976).

The results obtained for the individual constructs are shown in Table 2 below. The results in Table 3 are given as activity percentage of the individual CFDV constructs based on the activity of the CaMV 35S promoter construct (pRT 35S) which was set as 100%. The figures shown are the results of two or three independent experiments and also the mean of those results. The construct pRT CF XS contains the CFDV fragment first disclosed in German Patent P 43 06 832, which is not according to the invention and which is obtained by cleaving the CFDV DNA by means of the restriction endonucleases XhoI and StyI and additionally encompasses the translation start of the open reading frame ORF1.

TABLE 3

| Construct | Exp. 1 | Exp. 2 | Exp. 3 | Mean |
|---|---|---|---|---|
| pRT CF2 | — | 48 | 67 | 57.5 |
| pRT CF3 | 20 | — | 21 | 20.5 |
| pRT CF4 | 204 | 59 | 36 | 118 |
| pRT CF5 | 25 | 30 | 18.9 | 24.6 |
| pRT CF7 | 0 | 0 | — | 0 |
| pRT CF8 | 0 | 0 | — | 0 |
| pRT CF9 | 0 | 0 | — | 0 |
| pRT CF10 | 0 | 0 | — | 0 |
| pRT CF XS | 9 | 0.8 | 1.2 | 3.6 |
| pRT 35S | 100 | 100 | 100 | 100 |

As can be seen from the results shown in Table 3, the CFDV fragments contained in the constructs pRT CF 2–5 show a markedly higher promoter activity in tobacco protoplasts than the XhoI/StyI CFDV fragment promoter of the construct pRT CF XS, which additionally contains the translation start of the open reading frame ORF1 and has been described in German Patent P 43 06 832.

The constructs pRT CF 7–10 show no activity whatsoever in tobacco protoplasts, which demonstrates that the facility of forming the stem-loop structure in the region of the nucleotides 941 to 971 in the CFDV fragment promoter is essential for the promoter activity in plant cells.

In tobacco protoplasts, the construct pRTCF4 moreover shows a promoter activity which is comparable with that of the CaMV 35S promoter (cf. construct pRT 35S).

What is claimed is:

1. A method of using a coconut foliar decay virus (CFDV) DNA as a promoter for expressing genes in prokaryotes comprising, combining the CFDV DNA with an exogenous DNA forming a DNA construct, wherein the CFDV DNA comprises the sequence set forth in SEQ ID NO:1 or fragment thereof, thereof.

2. The method of claim 1 wherein the fragment is selected from the group consisting of nucleotides 211 to 991 of SEQ ID NO:1, 409 to 991 of SEQ ID NO: 1, 611 to 991 of SEQ ID NO:1, 711 to 991 of SEQ ID NO:1, 211 to 962 of SEQ ID NO:1, 409 to 962 of SEQ ID NO:1, 611 to 962 of SEQ ID NO:1, 711 to 962 of SEQ ID NO:1, and 1 to 1157 of SEQ ID NO:1.

3. The method of claim 1 wherein the CFDV DNA is selected from the group consisting of nucleotides 611 to 991 of SEQ ID NO:1 and 611 to 962 of SEQ ID NO:1.

4. The method of claim 1 wherein the prokaryote is a bacteria.

5. The method of claim 1 wherein the DNA constructs are suitable for transient and/or stable expression of genes.

6. A prokaryotic cell comprising the DNA construct of claim 1.

7. A method of using a CFDV DNA as a promoter for expressing genes in prokaryotes comprising combining the CFDV DNA with an exogenous DNA wherein the CFDV-derived DNA comprises the nucleotides 655 to 676, 682 to 701, 734 to 785, and 934 to 939 of SEQ ID NO:1.

8. A method of using a CFDV DNA as a promoter for expressing genes in prokaryotes or eukaryotes comprising, combining the CFDV DNA selected from the group consisting of nucleotides 211 to 991 of SEQ ID NO:1, 409 to 991 of SEQ ID NO:1, 611 to 991 of SEQ ID NO:1, 711 to 991 of SEQ ID NO:1, and 1 to 1157 of SEQ ID NO:1 with an exogenous DNA forming a DNA construct.

9. The method of claim 8 wherein the CFDV DNA is nucleotides 611 to 991 of SEQ ID NO:1.

10. The method of claim 8 wherein the eukaryote is a fungi.

11. A prokaryotic cell comprising the DNA construct of claim 8.

12. The method of claim 10 wherein the fungi is a yeast.

13. A method of using a fragment of CFDV DNA as a promoter for expressing genes in prokaryotes and eukaryotes comprising combining the fragment of CFDV DNA with an exogenous DNA wherein the fragment of CFDV DNA comprises the nucleotides 655 to 676, 682 to 701, 734 to 785, 934 to 939, and 941 to 971 of SEQ ID NO:1.

14. A method of using a CFDV DNA fragment as a promoter for expressing genes comprising, combining the CFDV DNA fragment with an exogenous DNA forming a DNA construct, wherein the DNA construct comprises the sequence of nucleotides selected from the group consisting of 211 to 991, 409 to 991, 611 to 991, 711 to 991, 211 to 962, 409 to 962, 611 to 962, and 711 to 962 set forth in SEQ ID NO:1.

* * * * *